United States Patent [19]

Shieh

[11] 4,003,793

[45] Jan. 18, 1977

[54] MEDIA CONTAINING MOLASSES AND SOY FLOUR FOR PRODUCING GLUCOSE ISOMERASE AND METHOD

[75] Inventor: Kenneth K. Shieh, St. Louis County, Mo.

[73] Assignee: Anheuser-Busch, Incorporated, St. Louis, Mo.

[22] Filed: Feb. 10, 1975

[21] Appl. No.: 548,432

[52] U.S. Cl. .......................... 195/66 R; 195/31 F; 195/62; 195/100

[51] Int. Cl.² ..................... C12D 13/10; C12B 3/04

[58] Field of Search ................. 195/31 F, 66 R, 62, 195/100, 101, 102, 65

[56] References Cited

UNITED STATES PATENTS

| | | | |
|---|---|---|---|
| 3,770,589 | 11/1973 | Heady et al. | 195/66 R |
| 3,795,585 | 3/1974 | Suzuki et al. | 195/65 |
| 3,813,320 | 5/1974 | Shieh et al. | 195/66 R |
| 3,834,988 | 9/1974 | Shieh et al. | 195/66 R |

OTHER PUBLICATIONS

Hamill, et al., "Antibiotic A4969 by Fermentation of Actinoplanes," Chemical Abstracts, vol. 77, p. 312, Abs. No. 138338n, (1972).

Takasaki, "Glucose Isomerase," Chemical Abstracts, vol. 79, p. 241, Abs. No. 135314g, (1973).

Tsumura, et al., "Cultivation Methods for Aerobacter Cloacae," Shokuryo Kenkyusho Kenkyu Hokoku, No. 19, pp. 189–193, (1965).

Primary Examiner—A. Louis Monacell
Assistant Examiner—Thomas G. Wiseman
Attorney, Agent, or Firm—Gravely, Lieder & Woodruff

[57] ABSTRACT

This disclosure relates to an improved medium for growing organisms (preferably *Actinoplanes missouriensis*) which produce glucose isomerase. Use of the medium results in increased yields of enzyme in shorter fermentation times. The improved medium contains molasses and particulate soy material, preferably soy flour.

7 Claims, No Drawings

MEDIA CONTAINING MOLASSES AND SOY FLOUR FOR PRODUCING GLUCOSE ISOMERASE AND METHOD

BACKGROUND OF THE INVENTION

In U.S. Pat. Nos. 3,813,320 and 3,834,988 (of which the applicant herein is a co-inventor), there are shown various media and various microorganisms which produce glucose isomerase. U.S. Pat. No. 3,813,320 involves the use of *Aerobacter levanicum* in a two-stage fermentation procedure using unpurified hardwood sulfite liquor as part of the medium in the second stage where the glucose isomerizing enzyme is produced. U.S. Pat. No. 3,834,988 shows the production of glucose isomerizing enzymes from an organism of the *Actinoplanes* genus in a medium whose principal constituent is corn steep liquor which has had the sludge removed. In the patent and scientific literature there are disclosures of other microorganisms which produce glucose isomerizing enzymes. Some of these enzymes convert D-glucose to D-fructose through one or more chemical intermediates (e.g. D-glucose-6-phosphate) but these enzymes do not appear to be practical for industrial use at the present time.

More promising are enzymes known as glucose isomerase that convert D-glucose to D-fructose directly. A number of these enzymes have been prepared from microorganisms of the genera *Lactobacillus*, *Pseudomonas*, *Pasteurella*, *Leuconostoc*, *Streptomyces* and *Aerobacter* (see review by Yamaka in Biochem. Biophys. Acta 154, 670–680 [1968]). In order that a significant quantity of glucose isomerase be formed by any of the foregoing microorganisms, xylose or xylan must be present in the growth medium to induce the enzyme. Pure xylose is relatively expensive, and when xylan is used in the growth medium, the microorganism must also produce enzymes capable of hydrolyzing the xylan.

In order to overcome the expense of growing the microorganism in a xylose or xylan containing medium, efforts have been expended to obtain a bacterium that will produce the enzymes constitutively. Lee, Hayes and Long (U.S. Pat. No. 3,645,848) have disclosed that certain strains of microorganisms belonging to the genus *Arthrobacter* are capable of producing enzymes that directly convert glucose or xylose to the corresponding ketose when grown in a medium in which xylose or xylan is absent. However, relatively small amounts of isomerase are produced and the growth medium requires relatively expensive nitrogen sources, such as yeast extract and meat protein.

REFERENCE TO PRIOR APPLICATIONS

In co-pending application Ser. No. 548,537 of Shieh entitled IMPROVED MEDIUM CONTAINING MOLASSES AND CORN STEEP LIQUOR FOR PRODUCING GLUCOSE ISOMERASE filed of even date herewith are disclosed media containing beet molasses, corn steep liquor and an inorganic nitrogen salt.

SUMMARY OF THE INVENTION

One of the principal objects of the present invention is to provide a method of growing microorganisms possessing enzymes for converting aldoses to ketoses using a medium which is relatively inexpensive and which results in good yields of enzyme.

This invention comprises a method of producing glucose isomerizing enzyme in a medium comprising molasses and soy flour. This medium has the advantage of not requiring filtration or purification to remove sludge as do media containing corn steep liquor.

Use of the present media also results in higher yields of enzyme compared to conventional media.

DETAILED DESCRIPTION

The following examples illustrate the present invention.

EXAMPLE NO. 1

Production of glucose isomerase from *Actinoplanes missouriensis* NRRL B-3342 and the effect of beet molasses and soy flour concentrations in the culture medium.

A. Preparation of inoculum

Inoculum was prepared by inoculating a culture of *Actinoplanes missouriensis* NRRL B-3342 into a 250 ml. Erlenmeyer flask containing 100 ml. of a sterile medium composed of the ingredients described in Table I.

TABLE I

| Ingredients | Amount (DSB) |
| --- | --- |
| Tryptone (Difco) | 1.7% |
| Soytone (Difco) | 0.3% |
| Glucose | 0.25% |
| $K_2HPO_4$ | 0.25% |

The medium was sterilized after the pH of the medium was adjusted to 7.1 with hydrochloric acid. The flask was inoculated with 5% inoculum (volume by volume) and incubated for 40 to 48 hours at 33° C. on a reciprocating shaker.

B. Production of the Enzyme

Production of glucose isomerase from *Actinoplanes missouriensis* NRRL B-3342 was carried out in 250 ml. Erlenmeyer flasks each containing 100 ml. of sterile medium. The media in a first set of six flasks were composed of 2% beet molasses, 0.15% dipotassium hydrogen phosphate, 0.05% magnesium sulfate heptahydrate. To a first flask soy flour was not added. To the other five, soy flour was added in the following quantities respectively: 0.5, 1.0, 1.5, 2.0 and 3.0 g. per flask.

The media in a second, third, fourth and fifth set of six flasks contained 3.0, 4.0, 5.0, and 6.0% beet molasses respectively, and the same amounts of ingredients as described in the first set of six flasks. Media containing no beet molasses, but 0.8, 3, and 7% soy flour also were prepared.

In preparing the foregoing described media, cane molasses or mixtures of cane and beet molasses can be used in place of beet molasses, but beet molasses is preferred.

The pH of the media was adjusted to 7.1 with hydrochloric acid prior to sterilization.

Each flask was inoculated with 8 ml. inoculum and incubated for 68 to 72 hours at 32° C. on a reciprocating shaker.

C. Determination of glucose isomerase activity

1. Harvest of cells

Cells are harvested from a culture by centrifugation at 10,000 times gravity for 15 minutes after the culture has been pasteurized at a temperature between 60° C. to 75° C. for 20 minutes at a pH between 7 and 9. The cells are washed once with tap water and dried at room temperature.

2. Extraction of cell-free enzyme

To 0.2 g. of dry cells is added 14 ml. of sodium phosphate buffer pH 7.0 (0.0375 M). The cell suspension is sonified at 4° C. for 4 minutes in Branson Sonifier J-17A. The cell-free extract is obtained by centrifugation at 27,000 times gravity for 15 minutes and used as a source of glucose isomerase.

3. Assay of isomerase activity

To each assay tube add 3.0 ml. of 1.33 M glucose solution buffered with 0.03 M sodium phosphate (pH 7.0), 0.2 ml. of salt solution composed of 0.06 M $MgSO_4 \cdot 7 H_2O$ and 0.006 M $CoSO_4 \cdot 7 H_2O$, and 0.5 ml. of 0.0375 M sodium phosphate buffer (pH 7.0). At zero time add 0.3 ml. of enzyme preparation to give a final volume of 4.0 ml. The reaction is carried out at 70° C. Aliquots are taken at 10, 15, 20 and 25 minutes and diluted in 0.02 M HCl.

The fructose content of the samples is assayed in an automatic analyzer by adapting the skatole-HCl method described by Pogell [J. Biol. Chem. 211:143 (1954)]. The color development is carried out at 52° C. as opposed to 37° C. Activity of glucose isomerizing enzyme is calculated from the slope and expressed in units (u). A unit of activity is defined as that quantity of enzyme which will produce 1 micromole of fructose from the glucose in 1 minute at 70° C.

D. Presentation of the results

Table II shows the effect of concentration of beet molasses and soy flour on the production of glucose isomerase from *Actinoplanes missouriensis*. The presence of soy flour in the growth medium in addition to molasses stimulates the growth of the organism as well as the enzyme production. The optimal concentrations of molasses and soy flour for the production of enzyme are 2 to 4% and 1 to 2% respectively. However, concentrations of molasses from 1% to 6% and concentrations of soy flour from 0.4% to 7% can be used. The organism can utilize soy flour as a sole source of carbon and nitrogen for growth and production of significant amount of glucose isomerase, but a combination of molasses and soy flour gives increased yields and is preferred.

The terms particulate soy material, soy flour, soy meal, etc., are used interchangeably throughout this application. Soy flour is generally considered to have a smaller average particle size than soy meal, but both are useful in this invention. Soy flour is preferred.

In addition to soy flour and molasses, it is preferred to have a nitrate source in the medium. The amount of nitrate is equivalent to that contained in $NaNO_3$ in a concentration of 0.1% to about 0.6% $NaNO_3$.

TABLE II

Effect of Beet Molasses and Soy Flour Concentrations on the Production of Glucose Isomerase by Actinoplanes Missouriensis

| Compositions of media | | Solids harvested (g/100 ml. cultures) | Sp. act. (u/g. dry solid) | Enzyme yields (u/ml. culture) |
|---|---|---|---|---|
| % beet molasses | % soy flour | | | |
| 2 | 0 | 0.21 | 2900 | 6.1 |
| 2 | 0.5 | 0.59 | 3926 | 23.2 |
| 2 | 1.0 | 0.83 | 4662 | 38.9 |
| 2 | 1.5 | 1.15 | 4550 | 52.5 |
| 2 | 2.0 | 1.23 | 4043 | 49.6 |
| 2 | 3.0 | 1.39 | 3744 | 52.0 |
| 3 | 0 | 0.30 | 3705 | 11.1 |
| 3 | 0.5 | 0.66 | 3777 | 24.8 |
| 3 | 1.0 | 0.89 | 4563 | 40.6 |
| 3 | 1.5 | 1.20 | 4342 | 52.0 |
| 3 | 2.0 | 1.29 | 3146 | 40.5 |
| 3 | 3.0 | 1.42 | 2691 | 38.2 |

TABLE II-continued

Effect of Beet Molasses and Soy Flour Concentrations on the Production of Glucose Isomerase by Actinoplanes Missouriensis

| Compositions of media | | Solids harvested (g/100 ml. cultures) | Sp. act. (u/g. dry solid) | Enzyme yields (u/ml. culture) |
|---|---|---|---|---|
| % beet molasses | % soy flour | | | |
| 4 | 0 | 0.21 | 3600 | 7.6 |
| 4 | 0.5 | 0.55 | 3510 | 19.3 |
| 4 | 1.0 | 1.05 | 4043 | 42.4 |
| 4 | 1.5 | 1.25 | 3887 | 48.5 |
| 4 | 2.0 | 1.14 | 2704 | 30.8 |
| 4 | 3.0 | 1.14 | 3538 | 40.2 |
| 5 | 0 | 0.32 | 3874 | 12.4 |
| 5 | 0.5 | 0.65 | 4388 | 28.4 |
| 5 | 1.0 | 0.83 | 4088 | 33.8 |
| 5 | 1.5 | 1.02 | 4232 | 43.0 |
| 5 | 2.0 | 1.10 | 3874 | 42.5 |
| 5 | 3.0 | 1.28 | 3504 | 45.0 |
| 6 | 0 | 0.34 | 3662 | 12.4 |
| 6 | 0.5 | 0.60 | 3835 | 23.0 |
| 6 | 1.0 | 0.80 | 3822 | 30.5 |
| 6 | 1.5 | 1.06 | 3738 | 39.6 |
| 6 | 2.0 | 1.02 | 3256 | 33.2 |
| 6 | 3.0 | 1.34 | 3120 | 41.6 |
| 0 | 0.8 | 0.21 | 6572 | 13.8 |
| 0 | 3.0 | 0.93 | 4320 | 40.0 |
| 0 | 7.0 | 1.46 | 2600 | 38.0 |

EXAMPLE NO. 2

Production of glucose isomerase from *Actinoplanes missouriensis* growing in a fermenter, and comparison of glucose isomerase production between cells growing in beet molasses-soy flour medium (BM-SF) and cells growing in beet-molasses corn steep liquor medium (BM-CSL).

A. Preparation of seed culture

The seed culture was prepared by inoculating a culture of *Actinoplanes missouriensis* into 1 liter Erlenmeyer flask containing 400 ml. of sterile seed media composed of the following ingredients described below in Table III.

TABLE III

| Ingredients | Amount (DSB) |
|---|---|
| Beet molasses | 1.0% |
| Soy flour | 0.4% |
| $Na_2HPO_4$ | 0.05% |
| $K_2HPO_4$ | 0.05% |
| $MgSO_4 \cdot 7 H_2O$ | 0.05% |
| pH | 7.1 |

The organism was grown for 48 hours at 33° C. on a reciprocating shaker.

B. Production of glucose isomerase in a fermenter

Glucose isomerase was produced by *Actinoplanes missouriensis* growing in a 14 liter fermenter containing 8 liters beet molasses-soy flour medium (BM-SF medium) or beet molasses-corn steep liquor medium (BM-CSL medium). The composition of BM-SF medium and BM-CSL medium were described in Table IV and Table V, respectively. The fermenter was made by the New Brunswick Co., New Brunswick, New Jersey.

TABLE IV

| Composition of BM-SF Medium | |
|---|---|
| Ingredients | Amount (DSB) |
| Beet molasses | 3.0% |
| Soy flour | 1.5% |
| Starch | 0.2% |
| $NaNO_3$ | 0.2% |
| $K_2HPO_4$ | 0.15% |

TABLE IV-continued

| Composition of BM-SF Medium | |
|---|---|
| Ingredients | Amount (DSB) |
| MgSO$_4$ . 7 H$_2$O | 0.05% |
| KCl | 0.025 % |
| FeSO$_4$ . 7 H$_2$O | 0.001% |
| DC Antifoam A | 0.05% |
| pH | 7.1 |

TABLE V

| Composition of BM-CSD Medium | |
|---|---|
| Ingredients | Amount (DSB) |
| Beet molasses | 3.0% |
| Corn steep liquor | 1.5% |
| Starch | 0.2% |
| NaNO$_3$ | 0.2% |
| K$_2$HPO$_4$ | 0.15% |
| MgSO$_4$ . 7 H$_2$O | 0.05% |
| KCl | 0.025% |
| FeSO$_4$ . 7 H$_2$O | 0.001% |
| DC Antifoam A | 0.05% |
| pH | 7.1 |

After the corn steep liquor was mixed with the beet molasses and the pH was adjusted to 7.1, the sludge of the corn steep liquor was removed by filtration.

The fermenter was sterilized for 60 minutes at 121° C. Fermentation was started by adding 10% seed culture into the medium in the fermenter. Aeration and agitation were set at 4 liter per minute or 0.4 vvm and 300 rpm respectively. Temperature was set at 33° C. The enzyme activity was determined according to the methods described in Example No. 1.

C. Presentation of results

Table VI shows the results concerning the yields of cells and enzyme from BM-SF medium and BM-CSL medium. The yield of enzyme is greater using BM-SF medium as compared to a BM-CSL medium. The medium of this invention is preferred over a corn steep liquor medium for *Actinoplanes missouriensis* because the medium does not have to be filtered to remove sludge as does a corn steep liquor medium.

TABLE VI

Comparative Study of Enzyme Yield in Fermenter Using Beet Molasses-Corn Steep Liquor Medium and Beet Molasses-Soy Flour Medium as a Fermentation Medium.

| | Beet Molasses-Corn Steep Liquor Medium | | | Beet Molasses-Soy Flour Medium | | |
|---|---|---|---|---|---|---|
| Fermentation Periods (hr.) | Solid Harvested (g. dry wt./100 ml. cult.) | Sp. act. (u/g. dry solid) | Enzyme Yields (u/ml. culture) | Solid Harvested (g. dry wt./100 ml. cult.) | Sp. act. (u./g. dry solid) | Enzyme Yields (u/ml. culture) |
| 24 | 0.63 | 3062 | 19.6 | 0.91 | 2665 | 24.6 |
| 48 | 0.94 | 3718 | 35.0 | 1.23 | 4400 | 54.0 |
| 60 | 0.90 | 4550 | 41.0 | 1.28 | 5252 | 67.0 |
| 72 | 0.87 | 4797 | 42.0 | 1.25 | 5398 | 67.5 |

Example No. 3

Effect of growth temperatures on the production of glucose from *Actinoplanes missouriensis*.

*Actinoplanes missouriensis* was grown in a 14 liter fermenter containing 8 l. beet molasses-soy flour medium at 28° C., 33° C. or 36° C. The composition of growth medium and fermentation conditions were similar to that described in Example No. 2. Table VII shows that the preferred temperature for production of the enzyme is at around 33° C., but at 28° and 36° C. the organism is also able to produce a good quantity of enzyme.

TABLE VII

Effect of Fermentation Temperature on the Yield of Glucose Isomerase
Fermentation Temperature (° C.)

| | 28 Growth Periods (hr.) | | | | | 33 Periods (hr.) | | | | | 36 Growth Periods (hr.) | | | | |
|---|---|---|---|---|---|---|---|---|---|---|---|---|---|---|---|
| | 24 | 36 | 48 | 60 | 72 | 24 | 36 | 48 | 60 | 72 | 24 | 36 | 48 | 60 | 72 |
| Solid Harvested g. dry wt./100 ml. cult. | 0.76 | 1.11 | 1.14 | 1.25 | 1.32 | 0.91 | 1.19 | 1.23 | 1.28 | 1.25 | 0.91 | 1.26 | 1.07 | 1.10 | 1.08 |
| Sp. act. u/g. dry solids | 1272 | 2778 | 3159 | 3452 | 3523 | 2664 | 3504 | 4400 | 5252 | 5398 | 2600 | 3250 | 4452 | 4641 | 5252 |
| Enzyme Yields u/ml. cult. | 14.2 | 30.8 | 36.0 | 43.0 | 46.5 | 24.6 | 41.6 | 54.0 | 67.0 | 67.5 | 23.9 | 41.0 | 47.0 | 51.0 | 56.7 |

I claim:

1. A method of making glucose isomerase comprising the steps of adding an inoculum of an organism belonging to the genus of *Actinoplanes* to a fermentor containing a medium composed of about 0.4% to about 7.0% particulate soy material selected from the group consisting of soy flour and soy meal as a growth nutrient, growing said inoculum for a period of time and at a temperature sufficient to produce a desired yield of glucose isomerase, and harvesting the glucose isomerase.

2. The method of claim 1 wherein the medium includes molasses.

3. The process of claim 2 wherein the molasses is selected from the group consisting of beet molasses, cane molasses, and mixtures of the two.

4. The process of claim 2 wherein medium includes about 1% to about 6% molasses, about 0.4% to about 7% particulate soy material and an amount of nitrate equivalent to that contained in NaNO$_3$ in concentration of about 0.1% to about 0.6% NaNO$_3$.

5. The process of claim 1 wherein the growth temperature is between 20° and 40° C.

6. The process of claim 1 wherein the growth temperature is between 30° and 34° C.

7. The process of claim 1 wherein the organism is *Actinoplanes missouriensis* NRRL-B 3342.

* * * * *